US009439869B2

(12) United States Patent
Ludwig et al.

(10) Patent No.: US 9,439,869 B2
(45) Date of Patent: Sep. 13, 2016

(54) NANOSHELLS ON POLYMERS

(71) Applicant: Abbott Cardiovascular Systems Inc., Santa Clara, CA (US)

(72) Inventors: Florian N. Ludwig, Hilversum (NL); Stephen D. Pacetti, San Jose, CA (US); Syed F. A. Hossainy, Hayward, CA (US); Dariush Davalian, San Jose, CA (US)

(73) Assignee: Abott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 14/086,907

(22) Filed: Nov. 21, 2013

(65) Prior Publication Data

US 2014/0377332 A1 Dec. 25, 2014

Related U.S. Application Data

(63) Continuation of application No. 13/623,818, filed on Sep. 20, 2012, now Pat. No. 8,592,036, which is a continuation of application No. 13/184,406, filed on Jul. 15, 2011, now Pat. No. 8,293,367, which is a continuation of application No. 11/473,822, filed on Jun. 23, 2006, now Pat. No. 8,017,237.

(51) Int. Cl.

| | | |
|---|---|---|
| *A61K 9/50* | (2006.01) | |
| *A61K 9/51* | (2006.01) | |
| *A61K 38/44* | (2006.01) | |
| *A61K 41/00* | (2006.01) | |
| *A61K 47/48* | (2006.01) | |
| *A61L 31/16* | (2006.01) | |
| *B01J 13/02* | (2006.01) | |
| *B22F 1/02* | (2006.01) | |
| *B82Y 5/00* | (2011.01) | |
| *A61K 9/00* | (2006.01) | |

(52) U.S. Cl.
CPC .......... *A61K 9/5031* (2013.01); *A61K 9/5115* (2013.01); *A61K 9/5138* (2013.01); *A61K 38/446* (2013.01); *A61K 41/0052* (2013.01); *A61K 47/48861* (2013.01); *A61K 47/48869* (2013.01); *A61K 47/48884* (2013.01); *A61K 47/48892* (2013.01); *A61L 31/16* (2013.01); *B01J 13/02* (2013.01); *B22F 1/025* (2013.01); *B82Y 5/00* (2013.01); *A61K 9/0004* (2013.01); *A61K 9/0019* (2013.01); *A61L 2300/00* (2013.01); *A61L 2400/06* (2013.01); *A61L 2400/12* (2013.01); *Y10S 977/773* (2013.01); *Y10S 977/906* (2013.01); *Y10T 428/2991* (2015.01); *Y10T 428/2998* (2015.01)

(58) Field of Classification Search
None
See application file for complete search history.

(56) References Cited

U.S. PATENT DOCUMENTS

| | | |
|---|---|---|
| 4,293,539 A | 10/1981 | Ludwig et al. |
| 4,622,244 A | 11/1986 | Lapka et al. |
| 4,897,268 A | 1/1990 | Tice et al. |
| 4,954,298 A | 9/1990 | Yamamoto et al. |
| 5,302,517 A * | 4/1994 | Rhode, III ............... 435/69.1 |
| 5,716,981 A | 2/1998 | Hunter et al. |
| 6,143,037 A | 11/2000 | Goldstein et al. |
| 6,160,084 A | 12/2000 | Langer et al. |
| 6,224,794 B1 | 5/2001 | Amsden et al. |
| 6,388,043 B1 | 5/2002 | Langer et al. |
| 6,528,093 B1 | 3/2003 | Camei et al. |
| 6,645,517 B2 | 11/2003 | West et al. |
| 6,656,506 B1 | 12/2003 | Wu et al. |
| 6,660,381 B2 | 12/2003 | Halas et al. |
| 6,685,986 B2 | 2/2004 | Oldenburg et al. |
| 6,692,466 B1 | 2/2004 | Chow et al. |
| 6,699,724 B1 | 3/2004 | West et al. |
| 6,767,637 B2 | 7/2004 | Park et al. |
| 7,048,947 B2 | 5/2006 | Camei et al. |
| 7,060,299 B2 | 6/2006 | Alavattam et al. |
| 7,223,282 B1 | 5/2007 | Hossainy |
| 8,017,237 B2 * | 9/2011 | Ludwig et al. ............. 428/403 |
| 8,048,448 B2 | 11/2011 | Ludwig et al. |
| 8,293,367 B2 * | 10/2012 | Ludwig et al. ............. 428/403 |
| 8,361,539 B2 | 1/2013 | Wu et al. |
| 8,592,036 B2 * | 11/2013 | Ludwig et al. ............. 428/403 |
| 8,603,530 B2 | 12/2013 | Ludwig |
| 8,603,536 B2 | 12/2013 | Wu et al. |
| 8,808,342 B2 | 8/2014 | Ludwig |
| 2002/0061363 A1 | 5/2002 | Halas et al. |
| 2002/0103517 A1* | 8/2002 | West et al. .................. 607/88 |
| 2002/0132045 A1 | 9/2002 | Halas et al. |
| 2002/0164064 A1 | 11/2002 | Karklin et al. |
| 2002/0187347 A1 | 12/2002 | Halas et al. |
| 2003/0082232 A1* | 5/2003 | Lee ........................ A61F 2/28 |
| | | 424/484 |

(Continued)

FOREIGN PATENT DOCUMENTS

| | | |
|---|---|---|
| WO | WO 99/46351 | 9/1999 |
| WO | WO 01/05586 | 1/2001 |
| WO | WO 2008/036144 A2 | 3/2008 |

OTHER PUBLICATIONS

HT Schmidt. "Calcium Phosphate Based Nanoshell for Use in Biomedical Applications." PhD Thesis, Notre Dame University, Mar. 2006, pages: Initial three pages, p. ii-xxvi, and pp. 1-319, resulting in 347 total pages in all.*

ML Immordino, F Dosio, L Cattel. "Stealth liposomes: review of the basic science, rationale, and clinical applications, existing and potential." International Journal of Nanomedicine, vol. 1(3), 2006, pp. 297-315.*

AV Kabanov, EV Batrakova, VY Alakhov. "Pluronic® block copolymers as novel polymer therapeutics for drug and gene delivery." Journal of Controlled Release, vol. 82, 2002, pp. 189-212.*

Albericio et al., "On the Use of PyAOP, a phosphonium salt derived from HOAt, in Solid-Phase Peptide Synthesis", Tetrahedron Letters vol. 38, No. 27, pp. 4853-4856 (1997).

(Continued)

*Primary Examiner* — Isaac Shomer
(74) *Attorney, Agent, or Firm* — Squire Patton Boggs (US) LLP

(57) ABSTRACT

Nano-constructs comprising nanoshells and methods of using the nano-constructs for treating or ameliorating a medical condition are provided.

11 Claims, No Drawings

(56) References Cited

U.S. PATENT DOCUMENTS

| | | | |
|---|---|---|---|
| 2003/0099630 A1 | 5/2003 | DiBenedetto et al. | |
| 2003/0147956 A1* | 8/2003 | Shefer et al. | 424/470 |
| 2003/0164064 A1 | 9/2003 | Halas et al. | |
| 2003/0170299 A1* | 9/2003 | Lee | A61K 9/1271 424/450 |
| 2005/0008572 A1* | 1/2005 | Prokop | A61K 9/5161 424/9.6 |
| 2005/0056118 A1 | 3/2005 | Xia et al. | |
| 2006/0079454 A1 | 4/2006 | Reches et al. | |
| 2007/0014752 A1 | 1/2007 | Roy et al. | |
| 2007/0053845 A1 | 3/2007 | Sengupta et al. | |
| 2007/0292495 A1 | 12/2007 | Ludwig et al. | |
| 2007/0292518 A1 | 12/2007 | Ludwig | |
| 2007/0298257 A1 | 12/2007 | Ludwig et al. | |

OTHER PUBLICATIONS

Berkland et al., "Fabrication of PLG microspheres with precisely controlled and monodisperse size distributions", J. of Controlled Release 73, pp. 59-74 (2001).

Berkland et al., "Precision Polymer Microparticles for Controlled-Release Drug Delivery", Am Chem. Soc. pp. 197-213 (2004).

Čeh et al., "Stealth liposomes: from theory to product", Advanced Drug Delivery Rev. 24, pp. 165-177 (1997).

Chang Dong et al., "Thermally Reversible Hydrogels: III Immobilization of Enzymes for Feedback Reaction Control", J. of Controlled Rel. 4, pp. 223-227 (1986).

Colombo et al., "Intracoronary Stenting Without Anticoagulation Accomplished with Intravascular Ultrasound Guidance", Circulation vol. 91, No. 6, pp. 1676-1688 (1995).

Crofford "Diabetes Control and Complications", Annu. Rev. Med. 46, pp. 267-279 (1995).

Ginsberg-Fellner, "Insulin-Dependent Diabetes Mellitus", pediatrics in review vol. 11, No. 8, pp. 239-248 (1990).

Hermanson Bioconjugate Techniques, book 11 pgs. (1996).

Hirsch et al., "Nanoshell-mediated near-infrared thermal therapy of tumors under magnetic resonance guidance", PNAS vol. 100, No. 23, pp. 13549-13554 (2003).

Meissner et al., "Intravascular Optical Coherence Tomography: Comparison with Histopathology in Atherosclerotic Peripheral Artery Specimens", J. Vasc. Interv. Radiol. pp. 343-349 (2006).

Musyanovych et al., "Grafting of Amino Functional Monomer onto Initiator-Modified Polystyrene Particles", Langmuir 21, pp. 2209-2217 (2005).

Oldenburg et al., "Infrared extinction properties of gold nanoshells", Applied Phys. Letters 75, No. 19, pp. 2897-2899 (1999).

Oldenburg et al., "Nanoengineering of optical resonances", Chem. Phys. Letters 288, pp. 243-247 (1998).

Polyethylene Glycol, product information, downloaded from: www.jtbaker.com/msds/englishhtml, 4 pgs., May 28, 2009.

Prakash et al., "Electrophilic Modification of Polystyrene Nanospheres", J. Nanosci. Nanotech. vol. 5, No. 3 (2005).

Ramos et al., "Modeling the emulsion polymerization of amino-functionalized latex particles", Polymer 47, pp. 1405-1413 (2006).

Ramos et al., "Polymeric and Colloidal Features of Latex Particles with Surface Amino Groups Obtained by Semicontinuous Seeded Cationic Emulsion Polymerization", pp. 3878-3886 (2005).

Targeting of Drugs 6, Strategies for Stealth Therapeutic Systems, Ed. By Gregoriadis and McCormack, pp. 139-145 and 4 title pages (1998).

Yoshida et al., "Modulating the phase transition temperature and thermosensitivity in $N$-isopropylacrylamide copolymer gels", J. Biomat. Sci. Polymer Edn. vol. 6, No. 6 pp. 585-598 (1994).

Hill-West, Jennifer et al. "Inhibition of thrombosis and intimal thickening by in situ photopolymerization of thin hydrogel barriers," Proc. Natl. Acad. Sci., vol. 91, 1994, pp. 5967-5971.

Hill-West, Jennifer et al. "Local Release of Fibrinolytic Agents for Adhesion Prevention," Journal of Surgical Research, 1995, vol. 59, 759-763.

International Preliminary Report on Patentability for PCT Application No. PCT/US2007/014657, filed Jun. 21, 2007, 6 pp.

International Search Report for related PCT Application No. PCT/US2007/014657, filed Jun. 21, 2007, 2 pp.

Pham, Tan et al. "Preparation and Characterization of Gold Nanoshells Coated with Self-Assembled Monolayers," Langmuir, 2002, vol. 18, pp. 4915-4920.

Sershen, S. et al. "Implantable, polymeric systems for modulated drug delivery," Advanced Drug Delivery Reviews, 2002, vol. 54, pp. 1225-1235.

Written Opinion of the International Searching Authority, for PCT Application No. PCT/US2007/014657, filed Jun. 21, 2007, 5 pp.

* cited by examiner

NANOSHELLS ON POLYMERS

RELATED APPLICATIONS

This application is a continuation of U.S. patent application Ser. No. 13/623,818, filed on Sep. 20, 2012, and issued as U.S. Pat. No. 8,592,036 B2 on Nov. 26, 2013, which is a continuation of U.S. patent application Ser. No. 13/184,406, filed on Jul. 15, 2011, and issued as U.S. Pat. No. 8,293,367 B2 on Oct. 23, 2012, which in turn is a continuation application of U.S. patent application Ser. No. 11/473,822, filed on Jun. 23, 2006, and issued as U.S. Pat. No. 8,017,237 B2 on Sep. 13, 2011, each of which is hereby incorporated by reference herein in its entirety.

BACKGROUND OF THE INVENTION

1. Field of the Invention

The present invention generally relates to a method of forming a nanoshell on a polymeric material, in particular a biodegradable polymeric material.

2. Description of Related Art

Nanoshell technology has attracted much attention because of the potential it offers in therapeutics with or without a therapeutic substance. For example, nanoshells have been demonstrated to absorb and convert light into heat, which can be used to offer local delivery of a drug or local treatment of an injury. Methods of forming nanoshells have been focused on forming them on a core material such as nanoparticulate inorganic ceramics or polymers such as polystyrene. For example, U.S. Pat. No. 6,685,986 is directed to a method of forming metal nanoshells upon a core substrate. The core substrate can be particles of silicon dioxide, titanium dioxide, poly(methyl methacrylate) (PMMA), polystyrene, gold sulfide, macromolecules such as dendrimers, and semiconductors such as Cd Se, Cd S, or GaAs. The particles can further have polyvinyl alcohol (PVA), latex, nylon, Teflon, acrylic, Kevlar, epoxy, glasses (col. 4, line 39 to col. 5, line 33). These core substrates, particularly those polymeric core materials, are generally non-degradable materials.

Therefore, there is a need for forming nanoshells upon a core material which is degradable.

The embodiments described below address the above-identified problems.

SUMMARY

The present invention provides a method of forming nanoshells on a polymeric core substrate. The nanoshell can be a thin layer formed on the polymeric core material. The nanoshell can have a thickness from about 5 nm to about 50 nm, e.g., about 5 nm to about 25 nm. The core substrate can have a size between about 100 nm to about 2000 nm, e.g., between about 100 nm and 150 nm.

The nano-constructs described herein have nanoshells formed on a core material. The nanoshells include a metal, carbon, or a conducting polymer. The nano-constructs can be administered to a target tissue of a subject, which can be human or an animal. An energy source can then be applied to the nano-constructs. The nano-constructs absorb the energy and then translate the energy into heat, thereby providing therapy to the subject.

In some embodiments, where the nano-constructs include one or more bioactive agents (e.g., a drug), the nano-constructs can convert energy into heat so as to cause the bioactive agents to be released. In some embodiments, the nano-construct can include a nanoshell that is porous to the bioactive agent or can be caused to form pores by heat generated by the interaction of the energy with the nano-construct. The nano-constructs can be used to treat or to ameliorate a vascular condition such as atherosclerotic plaque. Other vascular conditions that can be treated or ameliorated include, but are not limited to, vulnerable plaque, vascular inflammation, diffuse atherosclerotic disease, or restenosis.

DETAILED DESCRIPTION

The present invention provides a method of forming nanoshells on a polymeric core substrate. The nanoshell can be a thin layer formed on the core substrate formed of the polymeric core material. The nanoshell can have a thickness from about 5 nm to about 50 nm, e.g., about 5 nm to about 25 nm. The core substrate can have a size between about 100 nm to about 2000 nm, e.g., between about 100 nm and 150 nm.

The nano-constructs described herein have nanoshells formed on a core material. The nanoshells include a metal, carbon, or an electrically conductive, organic material such as graphite or a conductive polymer. The nano-constructs can be administered to a target tissue of a subject, which can be human or an animal. An energy source can then be applied to the nano-constructs. The nano-constructs absorb the energy and then translate the energy into heat, thereby providing therapy to the subject.

In some embodiments, where the nano-constructs include one or more bioactive agents (e.g., a drug), the nano-constructs can convert energy into heat so as to cause the bioactive agents to be released. In some embodiments, the nano-construct can include a nanoshell that is porous to the bioactive agent or can be caused to form pores by heat generated by the interaction of the energy with the nano-construct.

The nano-constructs can be used to treat or to ameliorate a vascular condition such as atherosclerotic plaque. Other vascular conditions that can be treated or ameliorated include, but are not limited to, vulnerable plaque, vascular inflammation, diffuse atherosclerotic disease, or restenosis.

In some embodiments, the nanoshells include a metal or an alloy. In some embodiments, the metal or metal alloy can include gold, silver, platinum, palladium, chromium, iridium, biodegradable metals such as iron, iron based alloys, magnesium, magnesium alloys, zinc, calcium, tungsten, alloys based on these metals, or combinations thereof.

In some embodiments, the nanoshells can comprise carbon. In some embodiments, the nanoshells can comprise an electrically conductive, organic material such as graphite or a conductive polymer. Conductive polymers can be, for example, poly(pyrrole), poly(thiophene), poly(acetylene), poly(aniline), graphite, carbon nanotubes, DNA or combinations thereof. The term conductive polymer can be used interchangeably with the term "conductive polymer." The nanoshell can comprise poly(L-lactide), poly-hydroxyalkanoate, polycaprolactone, or combinations thereof.

The nanoshells have a thickness in the range between about 2 nm and about 100 nm. Thickness of the shells and the ratio of core to shell dimension is relevant to the frequency of electromagnetic radiation or irradiation that the shells can absorb and translate into heat. For example, for nanoshells formed of a metal such as gold, the wavelength at which extinction efficiency is largest shifts to longer wavelengths as core-to-shell ratios increase, i.e. as shell thickness decreases if the outer diameter is kept constant.

Most relevant, the nanoshells can be designed such that they absorb radiation energy in the near-infrared spectrum between 650 nm and 900 nm which is permeable for tissue (see, e.g., Oldenburg S.J., et al., Applied Physics Letters; Vol. 75(19): 2897-2899; Oldenburg S.J., et al., Chemical Physics Letters 288:243-247 (1998)).

The nano-constructs described herein can be delivered to a subject for treating or ameliorating a vascular condition such as atherosclerotic plaque. Upon delivery, the nano-constructs can reach the target site via passive targeting or active targeting. Passive targeting can be achieved by extravasation of the nano-construct through leaky vasculature such as those present in atherosclerotic plaque. In some embodiments, the result of passive targeting can be assessed by the circulation time of the nano-constructs after delivery. Generally, the longer the nano-constructs remain in circulation, the more nano-constructs can reach the target site or target tissue, which sometimes is also referred to as the diseased site or diseased tissue. Therefore, in some embodiments, passive targeting can be enhanced by increasing nano-construct circulation times by rendering the surface of the nano-construct disguised using a compound such as poly(ethylene glycol). Other compounds that can be used to hide the nano-constructs include, but are not limited to, hyaluronic acid, phosphoryl choline, dextran, dextrose, sulfo betaine, polypyrrolidone, poly(2-hydroxyethyl methacrylate), albumin, poly(acrylic acid), and poly(methacrylic acid) and PVA.

Extravasation of the nano-constructs is also related to the position and nature of the diseased tissue. The capillary walls of tumor vasculature and the inflamed vasculature of diseased tissue is leaky compared to normal tissue. In some embodiments, extravasation can be achieved by circulation of the nano-constructs in the blood stream for a period from 10 minutes to 120 hours, more specifically from about 4 hours to 48 hours.

In some embodiments, the targeting can be achieved by active targeting. Active targeting can be carried out by attaching a targeting molecule on the nano-constructs (e.g., nanoshells). Targeting molecules include any peptide, antibody, or polysaccharide that has affinity to the target tissue or target site (e.g., atherosclerotic plaque). In some embodiments, the targeting molecule can be a surface-conjugated ligand to a receptor on an inflamed endothelium. Some examples of the targeting molecules are antibodies to CD34, RGD, YIGSR, peptides and antibodies to IIb/IIIa, heparin, hyaluronic acid, laminin, collagen, ICAM-1, ICAM-2, ICAM-3, fibrinogen, fibronectin, vitronectin, thrombospondin, osteopontin, integrins, VCAM-1, N-CAM, PECAM-1, IgCAM, folate, oligonucleotide aptamers, selectins, and cadherins.

The result of active targeting can be assessed by measuring the quantity of nano-constructs in the targeted tissue (i.e. vessel wall) versus the quantity administered. Similar to passive targeting, in some embodiments, the result of active targeting can be assessed by the circulation time of the nano-constructs after delivery. Generally, the longer the nano-constructs remain in circulation, the more nano-constructs can reach the target site. Therefore, in some embodiments, active targeting mediated by a targeting moiety can be enhanced by increasing nano-construct circulation times by modifying the surface of the construct using compounds such as poly(ethylene glycol), hyaluronic acid, phosphoryl choline, dextran, dextrose, sulfo betaine, poly(vinyl alcohol) (PVOH), polypyrrolidone, poly(2-hydroxyethyl methacrylate), albumin, poly(acrylic acid), poly(methacrylic acid) and PVA, whereby the organism's immunological processes fail to recognize the nano-construct as foreign.

Active targeting of the nano-constructs is also related to the position and nature of the diseased tissue. Nano-constructs can reach diseased tissue, which is highly vascularized, by systemic administration. Diseased tissue protected by the blood-brain barrier, which can prevent penetration of the nano-constructs, could be more advantageously accessed by administration into cerebro-spinal fluid. If a high concentration of nano-constructs is desired in the vessel wall of a portion of vascular system, then local delivery using a catheter may be suitable. Some target tissues such as the eye or prostate can be accessed externally by direct injection. In some embodiments, active targeting can be achieved by circulating the nano-constructs in the blood stream for a period from 10 minutes to 120 hours, more specifically from about 4 hours to 48 hours.

For those nano-constructs that include bioactive agents, the bioactive agent can be included in the core material in the form of core-material-drug matrix. Alternatively, the bioactive agent can be included in a substrate to which the nano-construct described herein is conjugated. For example, the substrate can be a nano- or micro- particle or capsule including the bioactive agent. The heat generated from the nano-construct can cause the bioactive agent to release from the substrate. The substrate to which the nano-construct is conjugated can be formed of the same of different material of the polymeric core material of the nano-construct. In some embodiments, the substrate is a self-assembled molecule such as liposomes containing phospholipids, micelles, or polymersomes. Examples of such self-assembled molecules include, but are not limited to, a liposome such as a small unilamellar vesicle (SUV), a large unilamellar vesicle (LUV), a polymersome, or hybrid vesicle comprising a polymer constituent(s), vesicle (LUV), a polymersome, or hybrid vesicle comprising a polymer constituent(s). Finally, the bioactive agent can be included in the shell of the nano-construct. Those of ordinary skill in the art recognize that these various locations for the bioactive agent are not exclusive. Thus, in some embodiments the bioactive agent can be present in any combination of core, substrate, or shell.

Polymeric Core Materials

The core material can be any polymeric material. Preferably, the core substrate can be formed of a material that comprises a biodegradable polymer. Also, it is preferable for the core polymeric material to have dielectric properties. In some embodiments, the core material can be a non-degradable polymer. As used herein, a degradable polymer is a polymer having a backbone that comprises at least one degradable linkage or grouping in the backbone, and a non-degradable polymer is a polymer having a backbone that lacks a backbone degradable linkage or grouping. Degradable linkages or groupings include a bond that can be cleaved by hydrolysis or enzymatic cleavage. An example of a degradable linkage or grouping is an ester linkage. An example of the non-degradable polymers is a polymer formed of vinyl monomers.

Representative polymeric core materials include poly (ester amide), polyhydroxyalkanoates (PHA), poly(3-hydroxyalkanoates) such as poly(3-hydroxypropanoate), poly (3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly (4-hydroxybutyrate), poly(4-hydroxyvalerate), poly(4- hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly (L-lactide), polyglycolide, poly(D,L-lactide-co-glycolide), poly(L-actide -co-glycolide), polycaprolactone, poly(lactide-co-caprolactone), poly(glycolide-co-caprolactone), poly(dioxanone), poly(ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. poly(ethylene oxide-co-lactic acid) (PEO/PLA)), polyalkylene oxides such as poly(ethylene oxide), poly(propylene oxide), poly(ether ester), polyalkylene oxalates, phosphoryl choline, choline, poly(aspirin), polymers and co-polymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants poly(ethylene oxide)-b-poly(propylene oxide)-b-poly(ethylene oxide) tri-block copolymers), poly(tetramethylene glycol), hydroxy functional poly(vinyl pyrrolidone), biomolecules such as collagen, chitosan, alginate, fibrin, fibrinogen, cellulose, starch, dextran, dextrin, hyaluronic acid, fragments and derivatives of hyaluronic acid, heparin, fragments and derivatives of heparin, glycosamino glycan (GAG), GAG derivatives, polysaccharide, elastin, or combinations thereof.

In some embodiments, the polymeric core material can exclude any one or more of the aforementioned polymers.

As used herein, the terms poly(D,L-lactide), poly(L-lactide), poly(D,L-lactide-co-glycolide), and poly(L-lactide-co-glycolide) can be used interchangeably with the terms poly(D,L-lactic acid), poly(L-lactic acid), poly(D,L-lactic acid-co-glycolic acid), or poly(L-lactic acid-co-glycolic acid), respectively.

In some embodiments, the core material can include ferromagnetic or magnetic ceramic particles.

Bioactive Agents

The nanoshells described herein can include one or more bioactive agent(s), which can be therapeutic, prophylactic, or diagnostic agent(s). These agents can have anti-proliferative or anti-inflammatory properties or can have other properties such as antineoplastic, antiplatelet, anti-coagulant, anti-fibrin, antithrombogenic, antimitotic, antibiotic, antiallergic, antifibrotic, and antioxidant. The agents can be cystostatic agents, agents that promote the healing of the endothelium such as NO releasing or generating agents, agents that attract endothelial progenitor cells, agents that promote the attachment, migration and proliferation of endothelial cells (e.g., natriuretic peptides such as CNP, ANP or BNP peptide or an RGD or cRGD peptide), while impeding smooth muscle cell proliferation. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Some other examples of the bioactive agent include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as anti-sense oligonucleotides, small interfering RNA (siRNA), small hairpin RNA (shRNA), aptamers, ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include 40-epi-(N1-tetrazolyl)-rapamycin (ABT-578), 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, or combinations thereof. Examples of cytostatic substances include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, pimecrolimus, imatinib mesylate, midostaurin, bioactive RGD, SIKVAV peptides, elevating agents such as cANP or cGMP peptides, and genetically engineered endothelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than non-therapeutic levels. The dosage or concentration of the bioactive agent can depend upon factors such as the particular circumstances of the patient, the nature of the trauma, the nature of the therapy desired, the time over which the administered ingredient resides at the vascular site, and if other active agents are employed, the nature and type of the substance or combination of substances. Therapeutically effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Methods of forming nanoshells

Nanoshells can be formed on a core material using established methods. For example, U.S. Pat. No. 6,699,724 describes forming conducting nanoshells on a non-conducting core. The size and thickness of the core/shell can be tuned so that the particles can absorb light with a desired wavelength. Biomolecules such as proteins or peptides can be attached to the nanoshells for binding to a specific tissue.

U.S. Pat. No. 6,685,986 describes a method of forming metal nanoshells upon a core substrate. The nanoshells can be formed of a metal such as gold or a conducting polymer. The core substrate can be particles of silicon dioxide, titanium dioxide, alumina, zirconia, poly(methyl methacrylate) (PMMA), polystyrene, gold sulfide, macromolecules such as dendrimers, semiconductors such as CdSe, CdS, or GaAs. The particles can further have polyvinyl alcohol (PVA), latex, nylon, Teflon, acrylic, Kevlar, epoxy, or glasses. Some other references, for example, U.S. application publication Nos. 2003/0164064, 2002/0061363, 2002/0187347, 2002/0132045, and 2005/0056118, also describes various methods of forming metal nanoshells on a core substrate. Formation of partial nanoshells can be according to the method described in, for example, U.S. Pat. No. 6,660,381.

In some embodiments, the nanoshells can be formed via metal colloidal nanoparticles such as colloidal gold nanoparticles. For example, colloidal gold nanoparticles of 3-4 nm size can assemble on nanoparticle surfaces functionalized by amine groups. These nanoparticles act as nucleation sites, and when a gold salt is present in a reducing environment, a solid gold shell can be formed around this type of nanosize template such as a nanosphere.

In some embodiments, polymeric nanoparticles such as commercially available polystyrene particles modified at their surface to present amine groups may be used as a template for gold nanoshells. Amine functionality can be placed onto these polymers by a variety of techniques. For example, polymeric surface can be modified to have amine functionality via plasma treatment in the presence of ammonia or hydrazine. This plasma process can be carried out on preformed nanoparticles by agitating them in a plasma reactor. Amino groups can also be incorporated into the end-groups of a polymer (e.g., a biodegradable polymer), if the initiator contains both a hydroxyl group and an amino group protected by a carbobenzoxy group or a t-butoxycarbonyl group, and this initiator is used to make a biodegradable polymer by ring opening polymerization, such as poly (L-lactide) or polyglycolide. After the polymerization, the protecting group can be removed, liberating the amino group. Polymeric methacrylates can be made with amino groups by using a monomer such as N-(3-aminopropyl) methacrylamide. A copolymer with other monomers such has butyl methacrylate or methyl methacrylate can be made. In some embodiments, a dispersion or emulsion polymerization process can be used to form monodisperse nanoparticles with surface amino groups (see, e.g., Ramos; Jose, Forcada; Jacqueline. Polymer 47(4):1405 (2006); Ramos; Jose, Forcada; Jacqueline, Polymer Chemistry 43 (17):3878 (2005); Prakash, G. K. et al., J. of Nanoscience and Nanotechnology 5(3):397 (2005); and Musyanovych, Anna; Adler, Hans-Jurgen Organic Chemistry III Macromolecular Society, 21(6):2209 (2005).

In some embodiments, the nanoshells can be formed via thiol-group-facilitated nanoparticle assembling. For example, biodegradable poly(propylene sulfide) can be produced in nanoparticle form as shown by Annemie Rehor (Ph.D. thesis, Swiss Federal Institute of Technology, Zurich, 2005). This polymer has thiol end-groups from the polymerization, which can be maximized in number by exposing the nanoparticles to reducing conditions.

In some embodiments, the nanoshells can be modified to include a targeting molecule. The target molecule can be any peptides or antibodies such as ligands for receptors on an inflamed endothelium. Examples of such targeting molecules include, but are not limited to, antibodies to CD34, RGD, YIGSR, peptides and antibodies to IIb/IIIa, heparin, hyaluronic acid, laminin, collagen, ICAM-1, ICAM-2, ICAM-3, fibrinogen, fibronectin, vitronectin, thrombospondin, osteopontin, integrins, VCAM-1, N-CAM, PECAM-1, IgCAM, folate, oligonucleotide aptamers, selectins, and cadherins.

Attachment of targeting molecule to nanoshells can be achieved by established methods. The targeting molecule can be attached to the nanoshell via covalent bonding or non-covalent interaction. Non-covalent interaction can be based on ionic interaction, hydrogen bonding or other type of interaction. For example, after formation of the gold nanoshell, molecules functionalized with a thiol group can be used to modify the nanoshell surface for targeting of the nanoshell, or to disguise the nanoshell surface. Thiol-terminated molecules have been shown to self-assemble on gold surfaces. For example, thiol-terminated poly(ethylene glycol) (PEG) having a molecular weight of about 200 Daltons to 10,000 Daltons, preferably between 500 Daltons to about 2,000 Daltons can be used to disguise the nanoshell surface. The other end of the PEG chain can be functionalized with a targeting molecule such as a peptide or an antibody to target the nanoshell to specific tissue within the body.

In some embodiments, the targeting molecule can be attached to a nanoshell via a spacer. A spacer molecule can be a short-chain alkyl group such as a C1-C20 alkyl, C3-C20 cycloalkyl, poly(ethylene glycol), poly(alkylene oxide). Other spacer molecules include dextran, dextrose, heparin, poly(propylene sulfide), hyaluronic acid, peptides, DNA, PVA and PVP.

Method of Use

The nano-constructs provided herein can be delivered or administered to a subject via any established mode of delivery. For example, the nano-constructs can be delivered by systemic delivery such as systemic injection. In some embodiments, the nano-constructs can be administered by local delivery such as direct injection. For disorders of the vascular system, the nano-constructs may be administered by catheter-based devices. These would include single and dual needle injection catheters, porous balloon catheters, balloon catheters with jets, and double balloon catheters. In general, the nano-constructs of this invention do not rely on any particular delivery method.

Upon delivery to the target tissue, an energy source can be applied to the nano-constructs. The nano-constructs can then absorb the energy and convert it or translate it to heat so as to warm or ablate the diseased tissue. The energy source can be in any form capable of reaching the nano-constructs and being absorbed and converted by the nano-constructs into heat. In some embodiments, the energy source can be applied through external radiation or through a catheter-based guidance system.

In some embodiments, the energy source is an electromagnetic radiation having a wave length from 500 nm to 1500 nm. For example, the energy source can be a near infrared radiation. In some embodiments, the energy source is a fluctuating electromagnetic field. Such electromagnetic field can have a frequency from $1 \times 10^6$ Hz to $6 \times 10^{14}$ Hz. In some embodiments, the electromagnetic field can have a frequency of 700 nm to 1300 nm where optical transmission is optimal (Welch A.; van Gemert, M. e. Optical-Thermal Response of Laser Irradiated Tissue, Plenum Press: New York, 1995).

In some embodiments, the energy source can be applied to the nano-constructs by a catheter-based fiber-optic. The localization of plaque can be imaged prior to the procedure or during the procedure by interrogation with an attenuated radiation. For example, the plaque may be imaged by optical coherence tomography using a wavelength of 1300 nm (Meissner O. A., et al. J Vasc Intery Radiol 2006; 17: 343-349) or intravascular ultrasound (Colombo et al., Circulation, 91:1676-88 (1995)). This same wavelength could then be used to apply energy to the nano-constructs after they are administered.

The nano-construct described herein can be used to treat, prevent or ameliorate a medical condition. Such a medical condition can be, e.g., a tumor or nephropathic kidney. In some embodiments, such a site can be a site of atherosclerosis. Other medical conditions treatable using invention processes or nanoconstructs include vulnerable plaque, diffuse atherosclerotic disease, diabetic retinopathy, aneurysm, anastomotic hyperplasia, claudication, chronic total occlusion, dysfunctional endothelium, recurring thrombus, fibrin accumulation, or combinations of these.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

We claim:

1. A nano-construct comprising:
   (a) a core material comprising a bioactive agent and a poly(ethylene oxide)-b-poly(propylene oxide)-b-poly (ethylene oxide) tri-block copolymer surfactant, and
   (b) a nanoshell formed around the core material, wherein the nano-construct is modified by attachment of phosphoryl choline, dextran, dextrose, albumin, or any combination thereof to the exterior surface of the nano-construct.

2. The nano-construct of claim 1, wherein the nanoshell comprises calcium.

3. The nano-construct of claim 2, wherein the nanoshell further comprises poly(L-lactide), polyhydroxyalkanoate, polycaprolactone, or a combination thereof.

4. The nano-construct of claim 1, wherein the nanoshell has a thickness between about 5 and about 25 nm.

5. The nano-construct of claim 1, wherein the nanoshell surrounding the core material is porous to the bioactive agent, and wherein the bioactive agent is selected from the group consisting of paclitaxel, docetaxel, estradiol, 17-beta-estradiol, nitric oxide donors, super oxide dismutases, 4-amino-2,2,6,6-tetramethylpiperidine-l-oxyl (4-amino-TEMPO), tacrolimus, dexamethasone, rapamycin, 40-O-(2-hydroxy)ethyl-rapamycin (everolimus), 40-O-(3-hydroxy) propyl-rapamycin, 40-O-[2-(2-hydroxy)-ethoxy]ethyl-rapamycin, 40-O-tetrazole-rapamycin, 40-epi-(N1-tetrazolyl)-rapamycin (ABT-578), hirudin, clobetasol, pimecrolimus, imatinib mesylate, midostaurin, and combinations thereof.

6. The nano-construct of claim 1, wherein the core material has a size in the range between about 150 nm to about 2000 nm.

7. The nano-construct of the claim 1, wherein the core material comprises ferromagnetic or magnetic ceramic particles, a peptide, a protein, or a combination thereof; and wherein if a peptide, a protein or a combination of a peptide and a protein is present, the bioactive agent comprises the peptide, the protein, or the combination of the peptide and the protein.

8. The nano-construct of claim 1, further comprising a substrate, the substrate being a small unilamellar vesicle (SUV), a liposome, a polymersome, or a hybrid vesicle.

9. The nano-construct of claim 1, further comprising:
   a targeting molecule on the exterior surface of the nano-construct, wherein the targeting molecule is a surface-conjugated ligand for receptors on an inflamed endothelium.

10. A method of treating or ameliorating a medical condition in a human being, comprising:
    delivering to a disease site in the body of the human being in need of treatment the nano-construct of claim 1, wherein the bioactive agent is a therapeutic agent.

11. The method of claim 10, wherein the disease is selected from the group consisting of tumors, nephropathic kidney, vascular conditions, atherosclerotic plaque, vulnerable plaque, vascular inflammation, diffuse atherosclerotic disease, restenosis, diabetic retinopathy, aneurysm, anastomotic hyperplasia, claudication, chronic total occlusion, dysfunctional endothelium, recurring thrombus, fibrin accumulation, and combinations thereof.

* * * * *